United States Patent [19]

Willer et al.

[11] 4,076,799
[45] Feb. 28, 1978

[54] METHOD OF INHIBITING SKIN IRRITATION

[75] Inventors: Sharon Gail Willer, Loveland; Paul Ronald Yust; Ralph Kelly, both of Cincinnati, all of Ohio

[73] Assignee: Cincinnati Milacron, Inc., Cincinnati, Ohio

[21] Appl. No.: 319,030

[22] Filed: Dec. 27, 1972

[51] Int. Cl.² ............... A61L 9/04; A61K 31/205; A61K 31/20; A61K 31/23
[52] U.S. Cl. ............................. 424/45; 424/244; 424/267; 424/274; 424/300; 424/303; 424/308; 424/312; 424/313; 424/316; 424/318; 424/320; 424/324; 424/325; 424/329; 424/330; 424/342; 424/343
[58] Field of Search ........................ 424/318, 45, 316

[56] References Cited

U.S. PATENT DOCUMENTS 3,538,009 11/1970 Kelly ........................ 424/318 X
3,630,934 12/1971 Kelly ........................ 424/343 X

*Primary Examiner*—Frederick E. Waddell
*Attorney, Agent, or Firm*—Plumley and Tyner

[57] ABSTRACT

A method of inhibiting or reducing the irritation of skin resulting from allergic contact dermatitis, caused by contact with natural or synthetic allergenic agents, e.g. poison ivy, and dinitrochlorobenzene, respectively, is described. The method comprises applying to the skin an irritating reducing effective amount of a protective agent which is an organic compound having at least two polar groups, e.g. carboxyl groups, separated by a chain of at least 15 atoms the majority of which are carbon atoms and optionally containing a cyclic moiety of at least 5 atoms, prior to contact of the skin with the allergenic agent. The protective agent may be combined in a pharmacologically acceptable base for application to the skin.

16 Claims, No Drawings

METHOD OF INHIBITING SKIN IRRITATION

BACKGROUND OF THE INVENTION

1. Field of the Invention

This invention relates to mitigating or reducing skin irritation in allergic contact dermatitis.

Contact dermatitis manifests itself in an inflamation of the skin. In mild cases the symptoms are itching, burning or reddening of the skin. In more severe cases vesiculation and edema may be present and may be followed by weeping and crusting. The most severe cases may be accompanied by bleeding vesicles and gross edema.

Contact dermatitis can be classified as allergic contact dermatitis or as primary irritant dermatitis. Although the symptoms of both types of dermatitis are similar there are some basic differences which are widely recognized.

Primary irritant dermatitis is the more common form of contact dermatitis and is caused by irritating agents which will cause dermatitis in all persons upon sufficient exposure. The period between contact with the primary irritant and the onset of symptoms is short or absent.

Allergic contact dermatitis may be caused by many substances which contact the skin. However, in this type of dermatitis a given substance may cause a dermatological reaction in certain subjects only. This reaction usually does not occur with the initial contact, but only upon subsequent exposures. Moreover, the reaction occurs only in these now "sensitized" subjects and there is a time interval between contact and developing of symptoms. Sensitization is caused by previous contact to the irritating substance. Some persons never become sensitized, others require numerous contacts and some require only a few contacts for sensitization. Thus, an essential difference is recognized between allergic contact dermatitis and primary irritant dermatitis, the latter being predictably induced by substances irritating to all persons the former being erratically induced, if at all, and only after sensitization.

Among the most common naturally occuring allergens capable of sensitizing and causing allergic contact dermatitis in a large proportion of subjects are the antigenic plants of the genus Rhus, such as poison ivy, poison oak, and poison sumac. The symptoms of reddening of the skin, formation of an itchy rash and often blistering of the skin common to all types of contact dermatitis are particularly familiar to many as a result of contact with poison ivy or other plants of the genus Rhus. Such dermatologic reactions are extremely irritating and in severe cases can cause temporary incapacitation of an individual. With the advent of the greater use of the outdoors by people, such as is experienced in camping, hiking, nature study and similar activities, especially in wooded or relatively less populated areas, the probability of contact with skin irritating plants is increased and therefore the need for protection against irritation resulting therefrom becomes apparent.

While allergic contact dermatitis due to poison ivy, poison oak, poison sumac and like antigenic plants is widely known it is equally well established that allergic contact dermatitis is caused by a large number of materials encountered by workers in industry. Such materials may be end products, raw materials, intermediates and by products of industrial processes. The problem of occupational allergic contact dermatitis is a significant one resulting in lost man hours of production, lost wages, discomfort to workers, job changes and workmen's compensation payments. Examples of materials known to cause allergic contact dermatitis among industrial and non-industrial workers are dinitrochlorobenzene, insecticides containing pyrethrum or Rotenone, dye intermediates such as aniline, nitro compounds, anthracene and derivatives thereof, benzidine and its compounds, naphthylamines and benzanthrone and its compounds, dyes such as paraphenylenediamine, aniline black, paramido phenol, amido-azo-toluene, amido-azo-benzene, Malachite Green, Metanil Yellow, Nigrosine and Rosaniline, photo developers such as hydroquinone, para-amido-phenol and pyrogallol, rubber accelerators and antioxidants such as hexamethylene tetramine, tetramethyl thiuram monosulfide, paratoluidine, phenyl beta naphthylamine and triethyl trimethyl triamine, coal tar and its derivatives such as pyridine and phenanthrene, explosives such as trinitrotoluol, tetranitro-methyl aniline, ammonium nitrate and sodium nitrate and synthetic and natural resins such as wood rosin and phenol formaldehyde.

2. Description of the Prior Art

It is known that protection against skin irritation can be achieved in subjects sensitized to allergens such as plants of the genus Rhus by exposing the subject to a controlled series of contacts with the allergenic irritant. The concentration of allergen, usually in an innocuous vehicle, in each subsequent controlled exposure can be increased so as to build-up a degree of immunity to the allergenic substance. Such a procedure results in temporary or partial protection against skin irritation caused by contact with the specific allergen or closely related allergens. However, the procedure, carried out under a physician's direction is somewhat tedious, inconvenient and often uncomfortable. Alternatively, the application of heretofor known lotions, creams and balms etc. to the skin prior to or even after contact with the skin irritant affords an ineffective method of preventing or reducing skin irritation due to many materials encountered by workers in industry and plants of the genus Rhus, such as poison ivy, poison oak and poison sumac.

It is also known that the degree of skin irritation caused by certain primary irritants, particularly organic detergents, can be prevented or reduced by incorporating agents called "mildness additives" by Kelly and Ritter in U.S. Pat. No. 3,630,934, issued Dec. 28, 1971, and in U.S. Pat. No. 3,538,009, issued Nov. 3, 1970. However, the Kelly and Ritter patents relate to reduction of the irritation from primary irritants and not to reduction of irritation from agents which cause allergic contact dermatitis following sensitization.

Accordingly, it was surprising to discover that certain compounds including the mildness agents mentioned in the Kelly Ritter patents mentioned above would also reduce skin irritation due to allergic contact dermatitis following contact of a sensitized object with allergens such as found in industry and genus Rhus plants.

OBJECT OF THE INVENTION

It is an object of this invention to reduce the amount of skin irritation due to allergic contact dermatitis caused by contact with an allergen following sensitization to that allergen.

Another more specific object of the present invention is to prevent or reduce skin irritation resulting from contact of the skin with irritating plants of the genus Rhus. Another more specific object of the present invention is to prevent or reduce skin irritation resulting from contact of the skin with allergenic agents formed or used in industrial processes.

It is a still further object of this invention to provide a method wherein lotion and cream compositions containing a protective agent are applied to the skin to prevent dermatologic reaction of the skin due to contact with skin irritating allergenic agents.

SUMMARY OF THE INVENTION

Broadly stated, this invention involves the application of skin irritating reducing effective amounts of compositions containing materials called "protective agents" to the skin prior to contact with agents capable of causing allergenic contact dermatitis, for example plants of the genus Rhus, to eliminate or reduce the dermatological reaction. The so-called "protective agent" can be generalized as an organic compound containing at least two polar groups which are separated by a chain of at least 15 atoms a majority of which are carbon atoms and optionally containing a cyclic moiety of at least 5 atoms. The protective agent may be dispersed or dissolved in a pharmaceutically acceptable base, such as the type used in hand lotions, hand creams and aerosol sprays, typically used for compositions intended for application to the skin.

As used herein, the term "polar group" is meant to define a group having a dipole amount and containing at least one nitrogen, oxygen, phosphorus, sulfur atom or combinations thereof. These groups are deemed to be capable of hydrogen bonding with the protein, although the formation of stronger bonds, such as covalent bonds, is not excluded. The optional cyclic moiety is preferably carbocyclic, i.e. cyclic hydrocarbon moiety of 5 to 18 carbon atoms which can be saturated or can contain from 1 to 9 double bonds and can contain one or more substituents on the ring. Heterocyclic moieties which contain the structures —O—, —S—, —N—, or —NH— in the ring can also be present in the protective agent and serve as the cyclic moiety.

In accordance with the method of the present invention, it has been discovered that the symptoms of allergic contact dermatitis caused by contact of irritating allergenic agents with the skin can be reduced or eliminated by applying to the skin the protective agent prior to contact with such irritating allergenic agents. Evidence, such as electrophoretic studies of mixtures of soluble proteins and protective agents indicates that some form of interaction occurs between the keratin layer of the skin and the protective agents. Although the complex formed between protein molecules and the protective agent can be isolated by the electrophoresis, the specific nature of the complex has not yet been established. It is presumed, however, that both adsorption and some form of chemical interaction are involved. It is further theorized that the chain of at least 15 atoms can aid in the adsorption of the protective agent onto the keratin layer of the skin and that the polar groups of the protective agent interact with the protein molecules of the keratin layer.

In addition to the requirement that the protective agent contain at least two polar groups, the polar groups of the protective agent must also be separated by a chain of at least 15 atoms, a majority of which should be carbon atoms. However, the presence of additional polar groups located intermediary to the described two terminal polar groups does not appear to interfere in the effectiveness of the protective agent. It is believed that as a result of this chain length the indicated polar groups are capable of, and do interact with different protein molecules.

The resulting irritation of the skin by an irritating agent is believed to be caused by the permeation of an irritating substance into either or both the pilosebaceous duct and/or the surface of the epidermis. The permeation through the pilosebaceous duct and/or the epidermis, causes damage to occur to the contacted viable cells of either or both anatomical sections of the skin. Further dermal insults are believed to result in the allergic syndromes which are manifested by so-called challenge dosages. The protective agents, employed in the methods of the present invention, are believed to counteract this permeating ability of the allergen. The protective agents are believed to provide additional bridges between the protein molecules of the keratin layer and/or pilosebaceous duct cells, thereby maintaining the integrity of the skin surface or duct wall. This in turn prevents the permeation of the irritating substance (allergen) to pass through these skin regions. It is to be understood, however, that we do not wish to be bound by the foregoing explanation of the activity of the protective agents of the method of the present invention, and that such explanation is only set forth for a better understanding of the present invention.

The protective agents utilized in the present invention are compounds which contain at least two polar groups separated by an organic radical of at least 15 atoms, a majority of which are carbon atoms. The organic radical separating the polar groups optionally contains a cyclic group. Additional polar groups may be present in this organic radical or may be located on branches attached to this radical. Such additional polar groups do not interfere in the effectivenes of the protective agent. The two polar groups described can be the same or different. Suitable polar groups include hydroxyl (—OH); carboxyl (—COOH); ester (R'O—CO—, wherein R' can be an aliphatic, cycloaliphatic, or aromatic radical of 1-12 carbon atoms, or can be part of a polyester chain; amino (—NH$_2$); substituted amino (NHR" or —NR"R'", wherein R" or R'" are aliphatic or aromatic hydrocarbon radicals of 1-12 carbon atoms, or wherein R" and R'" can combine to form 3-to 6-membered rings with the nitrogen, or wherein R" is part of a polyamine chain); amido

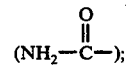

substituted amino

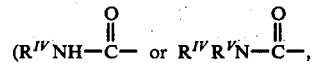

wherein $R^{IV}$ and $R^V$ are aliphatic or aromatic hydrocarbon radicals of 1-12 carbon atoms or wherein $R^{IV}$ and $R^V$ can combine to form 3 to 6 membered rings with the nitrogen or $R^{IV}$ can be part of a polyamide chain); quaternary ammonium salts

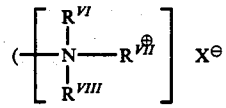

where $R^{VI}$, $R^{VII}$, and $R^{VIII}$ are lower alkyl radicals and $X^-$ is is an anion such as halogen ion); sulfate (—$SO_4ME$, where Me is a metal and preferably an alkali metal); sulfonate (—$SO_3Me$); sulfonamide (—$SO_2NH_2$); substituted sulfonamide (—$SO_2NHR^{IV}$ or —$SO_2NR^{IV}R^R$), thio acid salts (—COSMe); thioesters

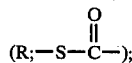

sulfoxides (=SO); sulfonic acid (—$SO_3H$); sulfinic acid (—$SO_2H$); phosphate (—$HMePO_4$ or —$Me_2PO_4$); and phosphonium salts (—$HPO_3Me$). The preferred polar groups employed in the protective agents of the method of the present invention are those which contain, aside from any metal or halogen which may be associated with the polar group in ionic form, carbon and oxygen or carbon and nitrogen. In general, functional groups of greater polarity are preferred over those of lesser polarity. It will be apparent that the size of any of the described substituents and particularly hydrocarbon substituents on the polar group will affect the polarity.

In general, the preferred substituents where aliphatic or aromatic radicals of 1–12 carbon atoms are mentioned, are those of fewest carbon atoms. For example, aliphatic radicals which are preferred are lower alkyl or alkenyl radicals containing 1–4 carbon atoms. As the aromatic radical phenyl is preferred and may be substituted with alkyl radicals of 1–4 carbon atoms. Aralkyl radicals, especially phenyl-lower alkyl radicals containing 1–4 carbon atoms in the lower alkyl group, are not excluded. Benzyl is the preferred aralkyl radical.

Aliphatic radicals of short or long chains containing water-solubilizing groups such as polyoxyalkylene groups, especially polyethylene glycol chains, are of considerable interest.

The presence of more than two polar groups each of which are separated by 15 or more atoms increases the effectiveness of a protective agent in which the polar groups are weak polar groups, such as hydroxyl groups, but does not appear to add significantly to the effectiveness of a protective agent containing at least two strong polar groups such as carboxyl groups separated by the necessary linking chain.

Although the minimum size of the linking radical is determined by the length of the chain separating the polar groups, the maximum size of the linking radical could be determined by the dispersibility or solubility of the protective agent in the medium in which it is incorporated. Thus, compounds which are not liquid or soluble or colloidally dispersible are not suitable in preventing allergic reactions Hence, the upper limit of the size of the linking radical is determined not only by the number of atoms in the linking radical, but also by the presence of additional polar groups in the linking radical which can increase the solublity or dispersibility of the protective agent, as well as the nature of any radical attached to the polar group. In general, however, the linking radical contains less than 80 atoms. As indicated, the linking radical has, preferably, a carbon backbone structure which can be aliphatic, cycloaliphatic, or aromatic in nature. The optional carbocyclic or heterocyclic moiety need not be part of the background structure. The linking radical can also be in the form of a polymeric structure such as a polyester, polyether, polyamide, or polyamide. Although other polymeric linking radicals will be apparent to those skilled in the art, many of these radicals are excluded by virtue of requirements such as liquid state, or solubility or collodial dispersibility.

The following classes of materials are protective agents suitable for use in the method of the present invention A. The unsaturated polymerized product obtained from the polymerization of 2 to 4 molecules of a monomeric ethylenically unsaturated $C_{12}$ to $C_{26}$ fatty acid or the saturated derivative product of said polymerized product, said product or derivative product containing 2 to 4 carboxyl groups; or in place of carboxyl groups derivative radicals selected from the group consisting of carboxyl salt; hydroxyl; unsubstituted amino; substituted amino wherein the substituents are aliphatic or aromatic hydrocarbon radicals of 1 to 12 carbon atoms, or said substituents taken together form a 3 to 6 membered carbocyclic or heterocyclic ring with the amino nitrogen; unsubstituted amido; substituted amido wherein the substituents are aliphatic or aromatic hydrocarbon radicals of 1 to 12 carbon atoms, or said substituents taken together form a 3 to 6 membered carbocyclic or heterocyclic ring with the amido nitrogen; quaternary ammonium wherein the nitrogen substituents are alkyl of 1 to 6 carbon atoms; lower alkyl ester; sulfate; sulfonate; phosphate, phosphonate; and derivative compounds containing further substituents in said alkyl, aliphatic or aromatic hydrocarbon radicals selected from the group consisting of carboxyl and the said derivative radicals.

Among the protective agents defined in A which can be utilized in the method of the invention are fatty polyquaternary ammonium compounds having the formula

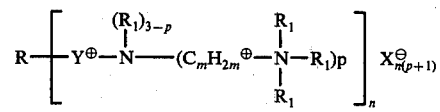

in which R is the hydrocarbon radical of the polymeric fatty acid, R (COOH)$_n$ obtained by polymerization of an unsaturated higher fatty acid containing 12 to 26 carbon atoms;

$R_1$ is an aliphatic hydrocarbon group having from 1 to 6 carbon atoms;

X is an anion;

Y is an alkylene radical having 1 to 8 carbon atoms;

$m$ is 3 to 4;

$n$ is 2 or 3; and $p$ is 0, 1 or 2.

The polymeric fatty acids from which the quaternary ammonium compounds employed as protective agents in the method of the present invention are derived are polymerization products of unsaturated fatty acids containing from 12 to 26 carbon atoms and generally having a degree of polymerization of two to four. Quaternary ammonium compounds prepared from fatty acid mixtures containing such dimer, trimer, or tetramer acids are also useful. Quaternary ammonium compounds of the type useful in the method of the present invention are disclosed in U.S. Pat. Nos. 3,073,864 and 3,299,138, the disclosure of which patents is incorporated herein by reference.

B. Condensation products of alkylene oxides having 2 to 4 carbon atoms and polyamides having 2 to 4 amino groups and containing 2 to 8 carbon atoms in an aliphatic, cycloaliphatic or aromatic group. The alkylene oxide units can be random or block units. Representative compounds of the above class found to be useful in this invention have the formula

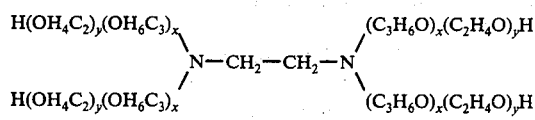

in which $x$ is from about 2 to 10, and $y$ is from about 2 to 15.

C. Condensation products of ethylene oxide with a hydrophobic base formed by the condensation of propylene oxide with propylene glycol, having the general formula

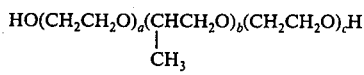

wherein
$a$ is 1 to 150;
$b$ is 15 to 70; and
$c$ is 1 to 150.

D. Esters and polyesters of cycloaliphatic or aromatic polycarboxylic acids containing at least one 5 to 7 carbon ring and a hydroxy compound selected from the group consisting of (a) polyoxyalkylene ethers containing 2 to 30 oxyalkylene units in which the alkylene radical contains 2 to 4 carbon atoms; and (b) condensation products defined in B and C above.

The benzene, naphthalene, cyclohexane, cyclopentane, cycloheptane and diphenyl polycarboxylic acids are suitable ring containing acids. Among the preferred polycarboxylic acids, are the corresponding dihydrobenzene (cyclohexadiene), tetrahydrobenzene (cyclohexene), polycarboxylic acids. The degree of polymerization can vary widely so long as the requirement that the compounds contain at least 15 carbon atoms between the polar groups and optionally the proper solubility or dispersibility characteristic in a pharmacologically acceptable base are maintained. The polyoxyalkylene ether can contain further substituents.

E. Esters and polyesters of the polymerized fatty acid product or the saturated derivative thereof defined in A above and a hydroxy compound selected from the group consisting of (a) polyoxyalkylene ethers containing 2 to 30 oxyalkylene units in which the alkylene radical contains 2 to 4 carbon atoms; and (b) condensation products defined in B and C above.

The most preferred protective agents are those of A above. Generally, the polymerized fatty acids contain from 2 to 4 monomeric acid units and, consequently, from 2 to 4 carboxyl groups. The polymeric fatty acids can be employed as protective agents, as such, or the carboxyl groups can be altered by known chemical reactions into other polar groups, such as by esterification, amidation, and the like. The polymerization of ethylenically unsaturated fatty acids into dimer, trimer, and tetramer acids is known in the art and the products are commercially available.

The polymerized fatty acids are products obtained by polymerizing 2 to 4 molecules of ethylenically unsaturated $C_{12}$ to $C_{26}$ fatty acid to give products containing 2 to 4 carboxyl groups comprising the dimer, trimer, tetramer or mixtures thereof, possibly containing some of the starting fatty acid in unpolymerized form. The starting ethylenically unsaturated acid can be mono- or polyunsaturated. Preferred polymerized fatty acids are obtained from linoleic acid. The dimer of linoleic acid is especially preferred. Where polyunsaturated acids are used to prepare polymerized fatty acids, it is believed that the resultant dimer, trimer, or tetramer contains unsaturation. These unsaturated polymerized fatty acids can be hydrogenated by known procedures to give the corresponding saturated dimers, trimers, tetramers or mixtures thereof. The saturated derivatives of polymerized fatty acids are also useful in this invention and are sometimes preferred, especially where color is important inasmuch as the saturated derivatives are often of a better, i.e. lighter, color than the corresponding unsaturated material.

Typical of the commercially available polymerized fatty acids useful in this invention are Empol ® Dimer Acids marketed by Emery Industries Inc. Literature supplied by Emery Industries Inc. indicates that reactions at the carboxyl group of Empol ® Dimer Acids are typical of aliphatic carboxylic acids. Indeed, this has been found to be true. Thus, the conversion of the carboxyl group to any of the other polar groups mentioned herein is rather simple and analogous to conversions used to prepare the corresponding derivatives of other carboxylic acids.

A number of patents teach methods of preparing polymerized fatty acids which are useful in this invention. Among these patents are U.S. Pat. Nos. 2,482,761, 2,793,219 and 3,157,681, the disclosure of which patents is incorporated herein by reference.

It will be apparent, in view of the foregoing discussion, that the protective agents need not be pure, but that a mixture of dimer and trimer acids, and that the protective agent can, furthermore, contain compounds, such as unpolymerized fatty acids, which do not add to the protective properties of the protective agent. Various polar groups can be substituted for the carboxyl groups of polymerized fatty acids as described above.

When the protective agent is placed in a pharmacologically acceptable base, the concentration of the protective agent in such compositions can vary widely, depending on the nature of the base in which it is dissolved or dispersed and other factors. Generally, concentrations of about 0.1 to 20% by weight of the weight of the base, more often about 0.5 to 10% by weight of the weight of the base, are used.

In one of the methods of this invention, the protective agent is incorporated into a pharmaceutically acceptable base to form a lotion or a cream. While there are a great many formulas for the production of such lotions or creams, most such compositions are emulsions comprising an emulsifier such as triethanolamine stearate or glycerol mono stearate; an emollient such as lanolin, cetyl alcohol, or stearyl alcohol; a humectant such as glycerine, sorbitol, mannitol, or the glycols, and various vegetable oils or perfuming agents. Although most creams and lotions today are of the emulsion type, the protective agents to be used in the method of our invention can also be added to the older hand balms formed of a gum, such as gum tragacanth, in water.

The protective agents used in the method of this invention can be incorporated into lotions or creams which contain other known protective agents, such as fatty acids for protection against dry dust, and petroleum jelly or waxes for protection against aqueous solutions; methyl cellulose and cellulose derivatives for protection against solvents, oils and fats.

The protective agents of this invention can also be incorporated into aerosol sprays and appropriate propellants, emulsifiers, emollients, humectants, perfuming agents and the like, as mentioned above, can be selected.

The following illustration is intended to show how potential protective agents are screened without actual use testing on human subjects.

ILLUSTRATION I

This illustration shows several of the methods which are used to determine whether a given chemical substance possesses activity as a skin protective agent and lists representative materials which have been determined to have such activity based on one or more of the described tests.

Several of the listed protective agents have been tested by each of the methods described below and a number of protective agents have been subjected to at least two of the tests. Good correlation of results has been found between the various tests. Good correlation has also been found between activity in the various tests and actual activity in reducing poison ivy (Examples 1 and 2) and in reducing irritation due to other allergenic agents such as dinitrochlorobenzene (Examples 3-4).

A. ANIMAL IMMERSION TEST

A female, albino guinea pig, weighing about 285 to 345 g, is immersed up to the thoracic region in the test solution at 40° C for 4.5 hours per day on three successive days. Each animal is thoroughly rinsed and dried after each immersion. Three days after the last immersions, the skin of each animal is examined for gross changes, and grades are assigned which represent the degree of damage to the skin. In general, three animals are tested simultaneously in the same solution. The grading system is based on a scale of 1 to 10, in which the numbers have the following meanings.

| Grade or Rating | Gross Reaction | Skin Damage |
|---|---|---|
| 1 | Severe cracking and bleeding; death of animal in most instances | Extremely severe; death of skin tissue |
| 2 | Severe cracking; moderate bleeding | skin tissue |
| 3 | Severe cracking; slight to moderate bleeding | Severe |
| 4 | Moderate cracking | " |
| 5 | Slight cracking | " |
| 6 | Severe scaling | Moderate |
| 7 | Edema; slight to moderate scaling | " |
| 8 | Slight scaling and moderate edema | Slight |
| 9 | Slight redness and edema | " |
| 10 | Normal | Normal |

Despite the fact that this exposure test is conducted using extremely dilute solutions, it is an exaggerated test, as compared to human exposure; although it has been established (see Canadian Pat. No. 639,398) that the test correlates extremely well with the skin irritation effect observed on human skin.

In preparing the test solution, a 100 g concentrate is first prepared which is then employed in the test solution in 1% by volume concentrations. In order to prepare a homogeneous concentrate which is readily dilutable, the following additional ingredients were added as indicated: Igepal CA-630, a commercially available nonionic wetting agent of octylphenoxypoly (oxyethylene) ethanol; triethanol amine, and capric acid. The triethanol amine (TEA) is employed to allow salt formation of mildness additives employed in combination with anionic detergents and the capric acid is employed for the same purpose in combination with cationic detergents. In general, the primary irritant and the protective agent are each employed in the examples illustrated below in a concentration of 15 weight percent based on the described 100 g concentrate.

A difference of about 2 units between the control animal (immersed in irritant) and the test animal (immersed in irritant containing protective agent) under the given conditions is generally considered to indicate a satisfactory protective effect.

A typical primary irritant used in the above-described test is sodium lauryl sulfate, but a variety of irritant materials have been used, including alkali, such as sodium and ammonium hydroxide. In general, a material which exhibits protective properties with a given primary irritant is found to exhibit similar properties with other primary irritants. Surprisingly, it has been found that protective agents effective against primary irritants are also effective against reducing irritation caused by allergens as in plants of the genus Rhus.

Further details of the above-described test are found in Ser. No. 696,509 filed Jan. 9, 1968, now U.S. Pat. No. 3,630,934, which is incorporated herein by reference.

B. OCCLUSIVE PATCH TEST (a modified version of the Finkelstein Patch Test)

Female albino guinea pigs, weighing between 300 and 350 grams are shaved, and one application of 7.4% formalin applied. A quantity of 0.15 milliliters of each protective agent is applied to part of the test area and rubbed into the skin approximately 10 times in each direction. After a drying time of one-half hour, a solution of the irritant is applied to a test pad which is placed over the test site and secured by tape. The pad and tape is then covered by a plastic sheet which is secured at the extremes of the abdominal area. 2.0 cc of trypan blue dye PPS was injected into each axilla of the test animal. After 18 hours, the pads were removed and the test sites examined for the degree of intensity of the dye which had accummulated at the test site. Dye accumulation was evaluated on the scale of 0 to 100, 0 being the intensity of dye when no protective agent was applied, and 100 being no visible dye accumulation. Variations of dye intensity of about 5% or more between test and control is considered significant. The following scale is also used to interpret results.

| Rating Scale (% Protectability) | |
|---|---|
| 80–100 | Excellent |
| 70–80 | Good |
| 60–70 | Minimal |
| 50–60 | Irritating |
| 0–50 | Very irritating |

C. ELECTROPHORESIS

The prescribed procedure for paper electrophoresis is followed. This involves placing a sample on a paper strip, mounting the strips is a closed cell filled with a buffer (pH 8.6 most often used), and connecting the apparatus to a power supply. Thus, degree of mobility of the sample along the strip in a given time can be measured. When applied to keratin, alone or in combination with protective agents or skin irritatnts or agents which degrade keratin samples, the degree of mobility indicates that an interaction takes place between protein and the protective agent, since this combination exhibits a mobility less than keratin alone. The combination of keratin and skin irritant or keratin and an agent which degrades protein, on the other hand, exhibits a mobility greater than protein alone. The differences in degree of mobility are indicative of the efficacy of the protective agent.

D. MICROSCOPIC STUDIES

Keratin, particularly hair, is subjected to a degradating agent with and without pretreatment with, or incorporation of, a potential protective agent. Protective qualities are evidence by reduced physical deterioration, especially scaling.

The following materials have been found to possess protective qualities for keratin by one or more of the methods described above. In the following formulae "D" is the divalent carboxyl free residue of polymerized fatty acids predominantly comprising dimerized linoleic acid. "T" refers to the trivalent carboxyl free residue of polymerized fatty acid predominantly comprising trimerized linoleic acid.

1. [D]─[CH$_2$OH]$_2$
2. [D]─[COOCH$_3$]$_2$
3. [D]─[CONH$_2$]$_2$
4. [D]─[CH$_2$NH$_2$]
5. 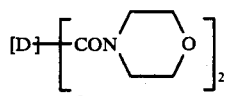
6. HO─[(CH$_2$─CH$_2$─O)$_m$─OC─[D]─CO$_2$]$_x$─H
   m = 2 to 30; x = 1 to 10
7. [D]─[CH$_2$─SO$_4$Na]$_2$
8. [D]─[CH$_2$─SO$_3$Na]$_2$
9. HOCH$_2$─[D]─COOH
10. Dimer acid or soap thereof
    [D]─[COO$^-$]$_2$ [X$^+$]$_2$ wherein X is H, Na, K, NH$_2$(C$_2$H$_4$OH)$_2$ or NH(CH$_2$CH$_2$OH)$_3$ 11. 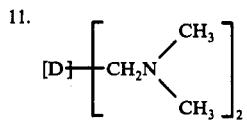

12. [D] ─ (CH$_2$─NH─CH$_2$─CH$_2$─NH$_2$)$_2$
13. [D] ─ (CH$_2$─NH─CH$_2$─CH$_2$─CH$_3$)$_2$
14. [D] ─ [CH$_2$PO(C$_4$H$_9$)$_3^+$ Br$^+$]$_2$

15. 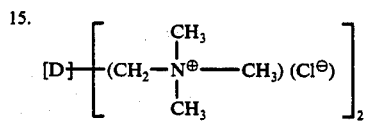

16. [T] ─ (COOH)$_3$
17. [T] ─ (CONH$_2$)$_3$
18. [T] ─ (COONa)$_3$
19. [T] ─ (SO$_4$Na)$_3$
20. [T] ─ (CH$_2$NH$_2$)$_3$

21. Reaction product of dimer acid and hydroxyethyl ethylene diamine. The product is shown as a diester of dimer acid and consists of a mixture of monoester, and half ester-half amide, diamide.

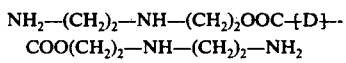

22. Diester of dimer acid and a polyoxyalkyleneated ethylenediamine

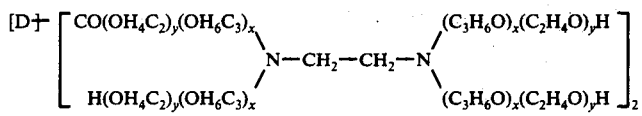

where x is from about 2 to 10; and y is from about 2 to 15.

23. Reaction product of dimer acid and N-amino-propyl diethanolamine. The product is shown as the diamide, but contains also the ester and esteramide.

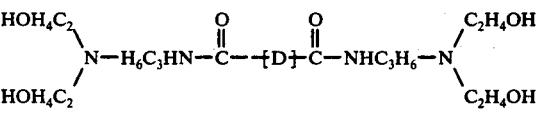

24. Di-ethanolamide of dimer acid.

[D]─[CONHC$_2$H$_4$OH]$_2$

25. Di-ester of dimer acid and ethylene glycol.

[D]─[COOCH$_2$CH$_2$OH]$_2$

26. Amide prepared from dimer diamine and acetic acid.

[D]─[CH$_2$NH COCH$_3$]$_2$

27. The reaction product of dimer acid and N-cyclohexyl-1, 3-propane diamine.

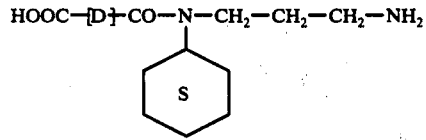

28. Polyethylene glycol ester of dimer acid.

[D]─[COO(C$_2$H$_4$O)$_x$H]$_2$ x = 2 to 30.

29. Carbitol diester of dimer acid.

[D]─[COO(C$_2$H$_4$O)$_z$C$_2$H$_5$]$_2$ z = 2 to 30.

30. Propylene glycol diester of dimer acid.

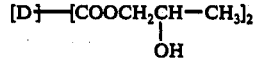

31. Dimer sulfate

[D]̵[CH$_2$SO$_4$H]$_2$

32. Polymeric ester of N,N-di(2-hydroxyethyl) aniline and dimer acid

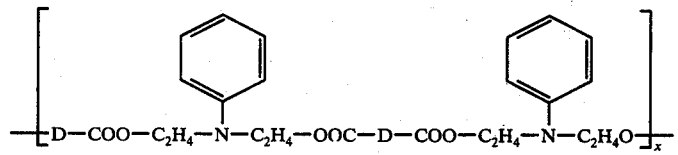

33. Octylphenoxypolyethoxyethanol diester of dimer acid.

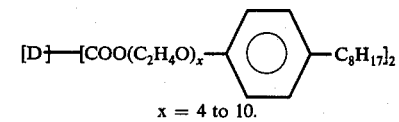

x = 4 to 10.

34. Polyester of polypropylene glycol and dimer acid.

[D]̵[COO(C$_3$H$_6$O)$_x$OC—D—COO(C$_3$H$_6$O)$_x$H]$_2$ x = about 6 to about 25

35. Polybutylene glycol diester of dimer acid.

[D]̵[CO(OC$_4$H$_8$)$_x$OH]$_2$ x = 10 to 20

36. Dimer glycol diacetate.

[D]̵[CH$_2$OOCCH$_3$]$_2$

37. N,N-bis-3-aminopropyl dimer diamine.

[D]̵[CH$_2$N(C$_3$H$_6$NH$_2$)$_2$]$_2$

38. Oleyloxypolyethoxyethanol diester of dimer acid.

[D]̵[CO(OC$_2$H$_4$)$_n$—O—(CH$_2$)$_8$—CH=CH(CH$_2$)$_7$CH$_3$]$_2$ n = about 10

39. Monostearyl-monopolyethylene glycol ester of dimer acid.

C$_{17}$H$_{35}$OOC—D—CO[OC$_2$H$_4$]$_x$OH x = about 9

40. [D]̵[CH$_2$—NHCH$_2$CH$_2$CH$_2$NH$_2$]$_2$

41. Mixed ester of reaction of pyromellitic anhydride with octylphenoxypolyethoxyethanol and subsequent reaction with the polyol resulting from reaction of ethylene and propylene oxides with ethylene diamine.

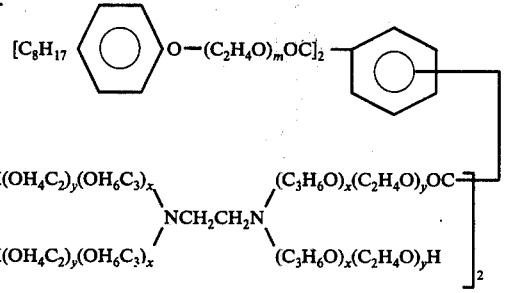

x = about 7; y = 9; m = 4 to 10.

42. Tetrakis-(3-carb-octylphenoxypolyethoxybenzoyl) ester of the tetrol resulting from ethylene oxide and propylene oxide addition to ethylene diamine.

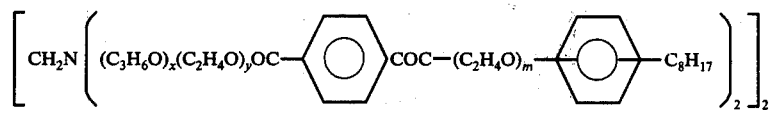

x = about 7; m = 4 to 10; y = about 9.

43. Polyethylene glycol diester of terephthalic acid.

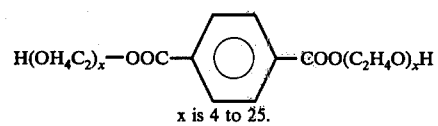

x is 4 to 25.

44. Polyethylene glycol diester of tetrahydrophthalic acid

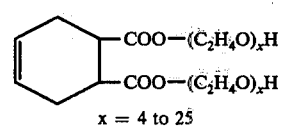

x = 4 to 25

45. Polypropylene glycol ester of pyromellitic acid

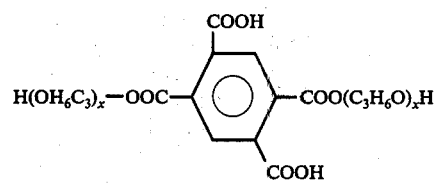

x = 5 to 8

46. Tris (octylphenoxypolyethoxyethyl) trimesate

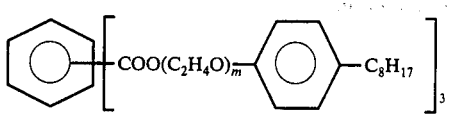

47. The tetrol resulting from block addition of propylene oxide and ethylene oxide to ethylene diamine.

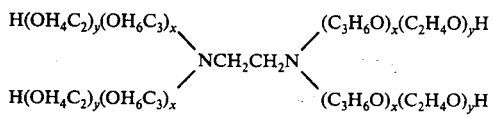

x is about 7
y is about 9

48.  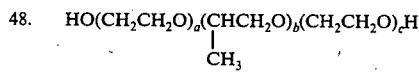

a = 1 to 150
b = 15 to 70
c = 1 to 150

PREFERRED EMBODIMENTS OF THE INVENTION

In a preferred embodiment, one of the protective agents falling within the described groups is incorporated into a standard cream base, lotion or aerosol which is applied to the skin prior to contact with the skin irritating plant. The protective agents falling within the disclosed groups which are currently most preferred are those based on dimerized fatty acids, specifically dimerized linoleic acid and the corresponding products obtained from hydrogenated dimerized linoleic acid. In particular, we have found that the dimerized acids which have been esterified with various alcohols, and particularly with oxyalkylene group-containing alcohols, are the most efficacious. However, since certain of the protective agents may display different degrees of success in protecting against various skin irritating allergenic agents our invention must be construed as encompassing the use of all of the compounds falling within the above-staged groups. While the examples below set forth the use of compounds which are effective against specific skin irritating allergenic agents, it should be understood that other compounds falling within the groups may be more effective against other skin irritating allergenic agents.

The following examples illustrate the invention and are not intended to be limiting in any manner.

EXAMPLE 1

This example illustrates the practice of the invention in reducing irritation of the skin by Rhus oleoresin (i.e. poison ivy extract). The reduction in irritation was demonstrated on the skin of volunteer male subjects in the following manner.

The test subjects were first titrated for sensitivity by applying to skin test sites graded concentrations of Rhus oleoresin in Hydrophilic Ointment U.S.P. A small quantity of the Rhus oleoresin containing ointment was applied to the skin by means of a spatula and the site covered by a gauze patch for 24 hours, after which the patch was removed and the site observed daily for the next several days. The concentration of Rhus oleoresin in the Hydrophilic Ointment which was chosen for subsequent work was that concentration which gave a brisk dermatitis at 48 hours. Upon completion of the titration for sensitivity, an ointment consisting of 5 to 10% by weight of bis(hydroxyethyl) dimerate in Hydrophilic Ointment was applied to a fresh skin test site by rubbing it on. The bis(hydroxyethyl) dimerate was prepared by esterifying a commercial product predominantly comprising dimerized linoleic acid with ethylene glycol in an acid-glycol ratio of about 1:2. This teatment was followed by the application, using a spatula, of the Rhus oleoresin containing ointment to the same site within 2 to 20 minutes after the application of the bis(hydroxyethyl) dimerate containing ointment. The site was then covered with a gauze patch for 24 hours after which the gauze patch was removed and daily observations made of the test site for the next 5 days. As a control a separate area of fresh skin was first treated by applying thereto the Hydrophilic Ointment alone (i.e. without the dimerate). This treatment was followed at 2 to 20 minutes thereafter by the application of the Rhus oleoresin containing ointment to the same area, by means of a spatula. A gauze patch was then placed over the area for 24 hours, after which the patch was removed and daily observations made for the next 5 days. The skin area to which the bis(hydroxyethyl) dimerate containing Hydrophilic Ointment had been applied prior to the application of the Rhus oleoresin containing ointment exhibited a marked reduction in dermatologic reaction as compared to the control area.

EXAMPLE 2

The procedure of Example 1 was followed except that an ointment consisting of 5 to 10% by weight of bis (triethanolamine salt) of dimer acid (dimerized linoleic acid) in Hydrophilic Ointment, instead of the bis(hydroxyethyl) dimerate, was applied to the skin by rubbing, prior to the application of the Rhus oleoresin containing ointment. Diminished reaction was observed in the skin area to which the bis(triethanolamine salt) of dimer acid containing ointment had been applied as compared to the control skin area.

EXAMPLE 3

This example was carried out using fresh male subjects and employing the procedure and materials of Example 1, except that dinitrochlorobenzene was substituted for the Rhus oleoresin. The results obtained were comparable to the results described in Example 1 with respect to the reduction of irritation.

EXAMPLE 4

The procedure and materials of Example 2 were employed on fresh male subjects except that dinitrochlorobenzene was substituted for the Rhus oleoresin. The results obtained were comparable to the results described in Example 2.

We claim:

1. A method for preventing or reducing irritation of the skin caused by contact with a skin irritating allergenic agent which comprises applying to the skin of a subject sensitized to said allergenic agent, prior to contact with said skin irritating allergenic agent, a protective agent containing at least two polar groups separated by a chain of at least 15 atoms, the majority of which are carbon atoms; wherein said protective agent is the unsaturated polymerized product obtained from the polymerization of 2 to 4 molecules of a monomeric ethylenically unsaturated $C_{12}$ to $C_{26}$ fatty acid or the saturated derivative product of said polymerized product, said polymerized product or saturated derivative thereof containing instead of 2 to 4 carboxy groups carboxyl salt groups; said irritation of the skin being an allergic contact dermatitis, said skin irritating allergenic agents being allergic contact dermatitis producing agents and said protective agent being present in an amount effective to reduce skin irritation compared to skin irritation produced in the absence of said protective agent.

2. The method of claim 1 in which said protective agent is the triethanolamine salt of dimerized linoleic acid or the corresponding saturated derivative.

3. The method of claim 1 in which said protective agent is the triethanolamine salt of dimerized linoleic acid.

4. The method of claim 1 in which said protective agent is dissolved or dispersed in a pharmacologically acceptable base in an amount ranging from about 0.1 to about 20 percent by weight of the weight of said base.

5. The method of claim 1 wherein the protective agent is applied to the skin in the form of an aerosol spray.

6. The method of claim 1 wherein said protective agent is applied to the skin in the form of a lotion.

7. The method of claim 1 wherein said protective agent is applied to the skin in the form of a cream.

8. The method of claim 1 wherein said skin irritating allergenic agents comprise antigenic plants.

9. The method of claim 8 wherein said plants comprise plants of the genus Rhus.

10. The method of claim 9 wherein said plants are poison ivy, poison oak and poison sumac.

11. The method of claim 1 wherein the said skin irritating allergenic agents are dyes and dye intermediates.

12. The method of claim 1 wherein the said skin irritating allergenic agents are insecticide compositions and components thereof.

13. The method of claim 1 wherein the said skin irritating allergenic agents are rubber accelerators and antioxidants.

14. The method of claim 1 wherein the said skin irritating allergenic agents are natural and synthetic resins.

15. The method of claim 1 in which said protective agent is the bis (triethanolamine salt) of dimerized linoleic acid.

16. The method of claim 1 in which said allergenic agent is detergent-free.

* * * * *